(12) United States Patent
Stordy et al.

(10) Patent No.: US 6,184,251 B1
(45) Date of Patent: Feb. 6, 2001

(54) USE OF ARACHIDONIC ACID AND/OR DOCOSAHEXANOIC ACID FOR THE TREATMENT OF DYSPRAXIA

(75) Inventors: Barbara Jacqueline Stordy, Guildford; David F. Horrobin, Stirling, both of (GB)

(73) Assignee: Scotia Holdings PLC, Stirling (GB)

( * ) Notice: Under 35 U.S.C. 154(b), the term of this patent shall be extended for 0 days.

(21) Appl. No.: 09/254,074

(22) PCT Filed: Aug. 26, 1997

(86) PCT No.: PCT/GB97/02282

§ 371 Date: Feb. 4, 2000

§ 102(e) Date: Feb. 4, 2000

(87) PCT Pub. No.: WO98/08501

PCT Pub. Date: Mar. 5, 1998

(30) Foreign Application Priority Data

Aug. 27, 1996 (GB) .................................. 9617847

(51) Int. Cl.⁷ .................................................. A61K 31/20
(52) U.S. Cl. ............................................................. 514/560
(58) Field of Search ............................................. 514/560

(56) References Cited

FOREIGN PATENT DOCUMENTS

| | | |
|---|---|---|
| 4304394A1 | 9/1993 | (DE) . |
| 0175468A2 | 3/1986 | (EP) . |
| 03477056A1 | 12/1989 | (EP) . |
| 0430870A1 | 6/1991 | (EP) . |
| 0454102A2 | 10/1991 | (EP) . |
| 0490561A2 | 6/1992 | (EP) . |
| 0585026A1 | 3/1994 | (EP) . |
| 0585027A1 | 3/1994 | (EP) . |
| 0615753A1 | 9/1994 | (EP) . |
| 0713653A1 | 5/1996 | (EP) . |
| WO94/28913 | 12/1994 | (WO) . |

OTHER PUBLICATIONS

M. Weller et al,: Very–Late–Onset Adrenoleukodystrophy: Possible Precipitation of Demyelination by Cerebral Contusion Neurology. vol. 42, No. 2, Feb, 1992, USA, pp. 367–370, XP002051780 see abstract.

*Primary Examiner*—William R. A. Jarvis
(74) *Attorney, Agent, or Firm*—Nixon & Vanderhye

(57) ABSTRACT

This invention relates to the administration of arachidonic acid or docosahexaenoic acid or precursors thereof to children or pregnant women for the treatment or prevention of dyspraxia.

6 Claims, No Drawings

USE OF ARACHIDONIC ACID AND/OR DOCOSAHEXANOIC ACID FOR THE TREATMENT OF DYSPRAXIA

This application is a 35 U.S.C. 371 filing of PCT/GB97/02282, filed Aug. 26, 1997.

FIELD OF INVENTION

This invention relates to fatty acids and their use.

GENERAL

Dyspraxia or apraxia, is a problem of human development, giving difficulty in planning and carrying out skilled non-habitual motor acts in the correct sequence (Fisher, Murray & Bundy, 1991). It is an impairment or immaturity of the organisation of movement, associated with which there may be problems of language, perception and thought. (Dyspraxia Trust 1995). Several different terms have been used to describe this disorder, Developmental Dyspraxia, Clumsy Child Syndrome, Minimal Brain Dysfunction, Perceptual Motor Dysfunction, Sensory Integrative Dysfunction, Motor Learning Difficulty. Apraxia, and Development Co-ordination Disorder. The term used in the Diagnostic and Statistical Manual of Mental Disorders DSM IV Washington, D.C. (American Psychiatric Association 1994) is Developmental Co-ordination Disorder., The World Health Organisation International Classification of Diseases Code (ICD-9-CM) is 315.4.

Dyspraxia is now recognised to be caused by an immaturity of brain development associated with poor synaptic transmission and possibly poor arborisation of neurones, that is to say a disorder with an organic basis.

In practical terms dyspraxics are poorly coordinated, disorganised, have problems of ideation. motor planning and execution so that written work and ball games are extremely difficult for them. Handwriting is poor. Poor memory, restlessness and impulsiveness may be features of the condition. Poor peer relations as a consequence of their clumsiness and slow learning of games lead to low self esteem.

FATTY ACIDS GENERALLY

The n-6 and n-3 essential fatty acids are related as below.

TABLE 1

| n-6 EFAs | | n-3 EFAs |
|---|---|---|
| 18:2n-6 | | 18:3n-3 |
| Linoleic acid (LA) | | α:-linolenic acid (ALA) |
| ↓ | δ-6-desaturase | ↓ |
| 18:3n-6 | | 18:4n-3 |
| γ-Linolenic acid (GLA) | | Stearidonic acid |
| ↓ | elongation | ↓ |
| 20:3n-6 | | 20:4n-3 |
| Dihomo-γ-linolenic acid (DGLA) | | Eicosatetraenoic acid |
| ↓ | δ-5-desaturase | ↓ |
| 20:4n-6 | | 20: 5n-3 |
| Arachidonic acid (AA) | | Eicosapentaenoic acid (EPA) |
| ↓ | elongation | ↓ |
| 22:4n-6 | | 22:5n-3 |
| Adrenic acid | | |
| ↓ | δ-4-desaturase | ↓ |
| 22:5n-6 | | 22:6n-3 |
| | | Docosahexaenoic acid (DHA) |

The acids, which in nature are of the all-cis configuration, are systematically named as derivatives of the corresponding octadecanoic, eicosanoic or docosanoic acids, e.g. z,z octadeca-9,12-dienoic acid or z,z,z,z,z,z docosa-4,7,10,13,16,19 hexaenoic acid, but numerical designations based on the number of carbon atoms, the number of centres of unsaturation and the number of carbon atoms from the end of the chain to where the unsaturation begins, such as. correspondingly, 18:2n-6 or 22:6n-3 are convenient. Initials, e.g. EPA and shortened forms of the names e.g. eicosapentaenoic acid, are used as trivial names in some of the cases.

PRESENT WORK

The invention is discussed in general terms later herein but broadly we have found dyspraxia to be due to inadequate supplies of the long chain polyunsaturated fatty acids docosahexaenoic acid (DHA) and arachidonic acid (AA). Dyspraxia may thus be treated by providing DHA and AA, the earlier the better. LA and especially GLA and DGLA are metabolic precursors of AA, and may be used in its stead. Likewise ALA and especially SA and EPA are precursors of DHA and may be used in its stead. Antioxidants may optionally be provided as well since they protect the highly polyunsaturated fatty acids and increase their incorporation into cell membranes.

DHA and AA are major constituents of the retina, of nerve tissue and of the brain. DRA is found in high concentrations at synapses and AA is important for cell signalling. Recent work has shown that their provision to children is important in the normal development of visual acuity, dark adaptation and cognitive function and is of particular benefit for dyslexics. However to our knowledge no one has previously suggested that dyspraxic individuals might also benefit from this treatment approach.

We first found a dramatic response to treatment with AA, DHA and GLA in a boy with dyspraxia. The subject was a 5 year old boy with severe dyspraxia. He exhibited all the classic signs of dyspraxia, he was clumsy, had poor balance and consequently bumped into objects and was accident prone. His drinks were always provided in a cup with a lid and a straw because of spillage. He did not enjoy and avoided drawing or learning to write because of poor fine motor skills and the difficulty of holding a pencil and physically drawing the lines as he wished. He had similar difficulty with scissors and cutting out. Clumsiness in ball games and difficulty with catching and hitting a ball lead to poor self esteem and difficulties in playing with friends. Characteristically at school he avoided the tasks which involved reading and writing and was easily distracted in class.

After supplementation with essential fatty acids and antioxidant for two months, his fine and gross motor skills and balance had improved so much that he rarely tripped over, he could carry liquid in an uncovered cup, and could catch a ball and hit a ball with a baseball bat. All these skills were absent before supplementation.

His language skills had also improved with more desire to read, fewer errors and faster reading. The social disruption in school caused by clumsiness and impulsiveness had also lessened. His teacher, unaware of the supplementation, reported that he was working well and was less disruptive. Overall the boy was calmer, happier and more willing to do things.

Following this success members of a local group affiliated to the Dyspraxia Foundation invited the applicants to test their children before and after supplementation with a mixture of n-3 and n-6 fatty acids. Seventeen families volunteered for this study. Informed consent was sought from the parents and children. All children completed the baseline assessment but two failed to attend for the final assessment. There were eleven boys and four girls with age range 5–12 years. Fine and gross motor skills were assessed using the ABC Movement Assessment Battery for Children (Henderson & Sugden 1992). The test consists of two parts, a check list, completed by an adult familiar with the child, and a series of objective measures of motor skills to assess manual dexterity, ball skills and static and dynamic balance. The check list examines the complex interactions between the child and the physical environment. It can be used on a one off basis to screen for children with problems or as in this study to evaluate intervention. The movement tests are also designed to be used to evaluate intervention. The test battery was completed at the outset and after 4 months supplementation with tuna oil, evening primrose oil, thyme oil and vitamin E. The supplement provided 480 mg DHA, 35 mg arachidonic acid, 96 mg gamma linolenic acid, 80 mg vitamin E and 24 mg of thyme oil daily.

There are other similar test batteries for movement assessment but this series was chosen because it is well established in use in several European countries and the USA and has been tested for reliability, validity, age and gender effects effects. It is used across the board to assess movement skills. The check list component can be used to screen children with movement problems. Children who fall on or below the $15^{th}$ percentile represent a marked degree of movement difficulty. Such children require further monitoring and assessment and may need immediate intervention. Children who fall on or below the $5^{th}$ percentile required detailed assessment and special consideration in terms of management and remediation programmes.

The objective measures of manual dexterity, ball skills and static and dynamic balance are summed to derive the Total Impairment Score (TIS). Percentile norms for TIS are used to assess severity of impairment, The cut off points are similar to those for the check list, $5^{th}$ and $15^{th}$ percentiles. If children fall on or below these percentiles intervention and remediation programs are required.

At the outset all children had checklist scores below the $15^{th}$ percentile indicating a marked degree of movement difficulty, This was confirmed by the objective measures of movement performance, Table 2. The Total Impairment Score, derived by summing scores for manual dexterity, ball skills and static and dynamic balance was below the $1^{st}$ percentile for 14 children and one child, age 12, was on the $8^{th}$ percentile. Scores are interpreted in forms of the norms expressed as percentiles. High scores in the table indicate poor performance. Manual dexterity, ball skills and static and dynamic balance were poor at baseline and improved following supplement (Table 2). Overall Total Impairment Scores and Check list scores improved significantly following supplementation (Table 2).

The parents completed a behaviour rating scale (Conners) for their children. There was evidence of reduced anxiety and improved behaviour following fatty acid supplementation (Table 3).

TABLE 2

ABC Movement Assessment Scores* (Mean ± SD) in 15 dyspraxic children before and after four months supplementation with n-3 and n-6 fatty acids

|  | Before | After | Paired t-test |
| --- | --- | --- | --- |
| Manual dexterity | 93 ± 2.85 | 6.95 ± 3.76 | <0.007 |
| Ball Skill | 6.03 ± 2.94 | 3.90 ± 2.13 | <0.002 |
| Static and dynamic balance | 8.23 ± 4.47 | 5.88 ± 4.09 | <0.03 |
| Total impairment score | 24.20 ± 6.83 | 16.73 ± 8.16 | <0.0001 |
| Checklist* | 87.14 ± 29.61 | 65.07 ± 28.63 | <0.001 |

High scores indicate poor performance
*Record incomplete for one child, n-14

TABLE 3

Conners Parent Rating Scale Scores in 15 dyspraxic children before and after four months supplementation with n-3 and n-6 fatty acids.

| | Adjusted means (±se) | | | p-values for improvement | |
| --- | --- | --- | --- | --- | --- |
| Category | Before | After | Improvement | Parametric | Non-parametric |
| Hyperactivity index | 13.27 | 11.07 | 2.20 (1.53) | 0.1711 | 0.4169 |
| Impulsive Hyperactive Scale | 5.33 | 4.40 | 0.93(0.57) | 0.1256 | 0.1365 |
| Psychosomatic Scale | 1.6 | 1.2 | 0.40(0.43) | 0.3726 | 0.4146 |
| Learning Scale | 8.67 | 7.13 | 1.54(0.88) | 0.1044 | 0.1216 |
| Conduct Scale | 3.87 | 3.73 | 0.14(0.89) | 0.8828 | 0.7861 |
| Anxiety Scale | 4.64 | 2.62 | 2.02(0.70) | 0.0116 | 0.0172 |
| All 48 Items | 45.04 | 35.45 | 9.59(4.05) | 0.0327 | 0.0353 |

Further studies on larger numbers of dyspraxics are in progress.

STATEMENT OF INVENTION

The invention is as set out in the claims herein but broadly we propose use of essential fatty acids, optionally in association with appropriate antioxidants, as highly beneficial in the treatment of dyspraxia and/or poor motor skills generally. Since dyspraxia is a disorder of development, and since it is a general principle of medicine that prevention is easier than treatment, we propose the approach as preventive in at risk situations by administration of fatty acids to children as babies or to their mothers in pregnancy.

Although AA and DHA are key fatty acids for the nerves and brain, the other n-6 and n-3 fatty acids derived from linoleic acid and alpha-linolenic acid (Table 1) are also important in these tissues. Because DHA and EPA (which is usually associated with DHA in fish oils) can inhibit conversion of linoleic to gamma-linolenic acid (GLA), it may be appropriate to provide with the DHA and AA, in some situations, supplements of GLA and/or DGLA as well, to prevent depletion of these important fatty acids. It may also be appropriate to provide EPA with the DHA. Furthermore the provision of antioxidants with the DHA and AA to protect the stability of the fatty acids in vivo may be appropriate. Some beneficial effects may accrue from giving either n-6 EFAs or n-3 EFAs alone, but because of the importance of both types of EFA in the central nervous system, both types, given together; are likely to give better results.

FORMS AND AMOUNTS

The fatty acids may be delivered in any appropriate form which can raise the levels of DHA, AA and/or the other fatty acids in the blood plasma and reference to fatty acids includes reference to them in such forms. Appropriate forms are the free fatty acids, their salts, including lithium salts, esters, amides alcohols, tri-, di- and monoglycerides, ascorbyl, meglumine and niacin derivatives, diesters and phospholipids such as phosphatidylcholine or phosphatidylethanolamine or any other appropriate carrier.

The fatty acids are not toxic and so they may be given in doses of from 1 mg to 100 g per day, preferably 20 mg to 10 g and very preferably 50 mg to 2 g/day, formulations suitably being provided to give convenient divided doses. They may be administered orally, enterally, parenterally or topically by any appropriate formulation including fortification of conventional foods, capsules, pastilles, tablets, powders, emulsions, suspensions, oils, creams, lotions, patches, liposomes, galactolipid based preparations or any other form known to those skilled in the art.

FORMULATION EXAMPLES

The ratio of n-3, particularly DHA, to n-6 acids in the formulation, where both are used, may range from 1-100 to 100-1, preferably 5-1 to 1-5 and very preferably 3-1.

The following may be used for the purposes discussed as above.

1. 500 mg capsules containing 100 mg DHA, and 10 mg AA optionally with 50 mg GLA in an appropriate carrier oil to be taken at a dose of 4 capsules/day in children and 8 capsules/day in adults.
2. As in 1 but with the inclusion of an appropriate antioxidant or antioxidant mix such as 10 mg vitamin E, thyme oil or oregano oil.
3. An emulsion for oral, enteral or intravenous use providing in each Iml of emulsion 400 mg of oil containing 80 mg of DHA, 20 mg of AA and optionally 20 mg of GLA.
4. A topical patch providing 50 mg of AA and 50 mg of DHA for trans-cutaneous administration.
5. A milk based drink providing in each 200 ml of drink 400 mg DHA, 40 mg AA and optionally 200 mg GLA.
6. A milk based drink providing in each 200 ml of drink 400 mg DHA, 200 mg GLA and 40 mg AA and optionally 200 mg GLA with the inclusion of an appropriate antioxidant or antioxidant mix such as 10 mg vitamin E, thyme oil or oregano oil.

USE EXAMPLES

Examples of administration of formulations are effectively given in the account of the work with children given earlier herein.

What is claimed is:

1. A method of preventing or treating dyspraxia, poor fine and gross motor skills in dyspraxia or poor fine and gross motor skills in non-dyspraxic individuals comprising administering to children or pregnant women an effective amount of arachidonic acid (AA) or docosahexaenoic acid (DHA) or both or a precursor fatty acid thereof.

2. The method of claim 1 for prophylaxis wherein children are treated between birth and the age of one year.

3. The method of claim 1 or claim 2 wherein the precursor fatty acid is selected from the group consisting of AA, and ALA and DHA.

4. The method of claim 3 wherein the fatty acid precursor for AA is GLA or DGLA and the precursor fatty acid for DHA is SA or EPA.

5. The method of claim 1 or 2 wherein GLA or DGLA is administered in addition to AA.

6. The method of claim 1 or 2 wherein a pharmaceutically acceptable antioxidant for the fatty acids is also administered.

* * * * *